(12) United States Patent
Makk et al.

(10) Patent No.: US 6,815,465 B1
(45) Date of Patent: Nov. 9, 2004

(54) HETEROCYCLIC COMPOUNDS INHIBITING ANGIOGENESIS

(75) Inventors: Nándor Makk, Kismaros (HU); Gábor Ambrus, Budapest (HU); AnikóTegdes, Budapest (HU); András Jeney, Telki (HU); Ferenc Timár, Budapest (HU)

(73) Assignee: IVAX International GmbH, Rapperswil (CH)

( * ) Notice: Subject to any disclaimer, the term of this patent is extended or adjusted under 35 U.S.C. 154(b) by 1 day.

(21) Appl. No.: 10/048,659

(22) PCT Filed: Aug. 2, 2000

(86) PCT No.: PCT/HU00/00088

§ 371 (c)(1),
(2), (4) Date: Jun. 3, 2002

(87) PCT Pub. No.: WO01/09113

PCT Pub. Date: Feb. 8, 2001

(30) Foreign Application Priority Data

Aug. 2, 1999 (HU) .............................................. 9902628

(51) Int. Cl.[7] .............................................. A61K 31/445
(52) U.S. Cl. ........................................ 514/519; 514/529
(58) Field of Search .................................. 514/519, 629

(56) References Cited

FOREIGN PATENT DOCUMENTS

| JP | 08 173176 A | | 7/1996 |
|---|---|---|---|
| JP | 08-173176 | * | 7/1996 |
| JP | 09 227549 A | | 9/1997 |

OTHER PUBLICATIONS

Keller–Schierlein, Helvetica CHimica Acta., vol. 50(3), pp. 731–753, 1967.*
Keller–Schierlein, CA 65:56510, abstract of Experientia, vol. 22(6), 355–359, 1966.*
Wakabayashi, Toshiaki, et al.: Borrelidin is an angiogenesis inhibitor; J. Antibiot. (1997), 50 (8), 671–676.
Keller–Schierlein, W.: Stoffwechsekprodukte von Mikroorganismen Uber die Konstitution des Borrelidins; Helvetica Chimica Acta. (1967) 50 (3), 731–753.

* cited by examiner

Primary Examiner—D. Margaret Seaman

(57) ABSTRACT

The invention relates to compounds of general formula (I) wherein R stands for a group of general formula —COOR$^1$, —CONR$^2$R$^3$, —CONR$^4$CONR$^4$R$^5$ or —CH$_2$OR$^6$, wherein R$^1$ stands for a C$_{2-6}$ alkyl group; a C$_{1-6}$ alkyl group substituted; or a C$_{3-6}$ cycloalkyl group; R$^2$ and R$^3$ are identical or different and stand independently from each other for hydrogen atom or a C$_{1-6}$ alkyl group which optionally may be substituted; a 5- or 6-membered cycloalkyl or a heteroaryl group; and their tautomers, solvates and the mixtures thereof and acid addition salts of these compounds. The invention also relates to pharmaceutical compositions comprising compounds of general formula (I) as active agent. The angiogenesis-inhibitors according to the invention inhibit the neovascularization in living tissues and as such can be used for preventing and inhibiting angiogenesis appearing in connection with tumor growth and for preventing the formation of tumor metastases.

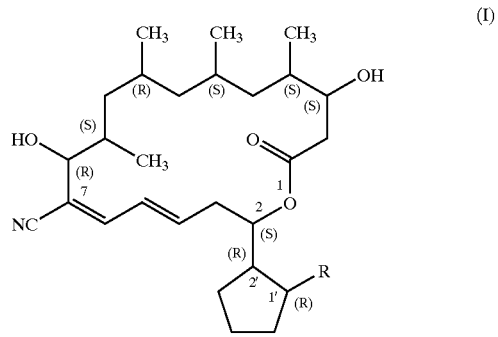

7 Claims, No Drawings

HETEROCYCLIC COMPOUNDS INHIBITING ANGIOGENESIS

This invention relates to novel borrelidin derivatives, more specifically to novel borrelidin derivatives prepared by transforming the carboxyl group on the cyclopentane ring of borrelidin. Furthermore, the invention relates to pharmaceutical compositions containing such compounds and to the use of these compounds for preparing pharmaceutical compositions.

The novel compounds according to the invention show valuable biological efficiency, namely they have remarkable angiogenesis-inhibiting effect and antimetastatic action.

It is known that the angiogenesis is a phenomenon where blood-vessels are formed in the organism and a new vascular system is formed. The angiogenesis has very different forms depending on the growth and function of the endothelial cells, by all means it can be considered as a certain kind of cascade reactions. The angiogenesis takes place under normal physiological circumstances like a part of the evolution and reproduction processes in the case of the embryo, foetus, placenta, uterus and similar organs. It may be, however, a part even of a pathological process which accompanies the wound healing, infection as well as tumour growth, furthermore promote the formation of tumour metastases.

From the literature the clinical observation is known for a long time that the majority of cancer tumorous patients die due to metastases. This situation has been improved in the recent years by the radiation therapy and chemotherapy but the results attained are by no means reassuring.

Owing to the results attained while studying the pathobiological features of the malignant diseases, in the last years a new trend of antitumour drug research has developed. It can be attributed to this new tendency that nowadays the planning of novel active agents is directed, besides the research of active agents inhibiting the growth of tumorous tissues, even towards other pathobiological events (immortalisation, metastases, apoptosis, angiogenesis) responsible for maintaining the malignity. From these events special attention deserves the neovascularisation (formation of novel blood-vessels) which ensures continuous blood supply for the growing tumours, since in lack of same the tumorous cells are killed. According to the conclusions of tumour-biological examinations the progression of malignant diseases can be considered to be a function of angiogenesis, and the transition of the premalignant period into the invasive period, further the induction of the dormant state of the tumorous cell population in direction of proliferation can be brought into close connection with the formation of blood vessels.

Thus, the drug research of antitumorous agents is aimed today at planning and developing molecules having novel points of attack, by the aid of which the healing of cancer can be rendered more efficient than before.

Among these novel molecules priority is given to the group of antiangiogenetic agents which, by inhibiting the neovascularization and consequently the formation of metastases, may open a new period in the therapy of tumorous diseases.

Several compounds are known for having angiogenesis-inhibiting effect. From these compounds the following are enumerated as examples, without being exhaustive: angiostatic steroids [Folkman, J. et al., Science 221, 719 (1993)] like the cortisone which inhibits the function of the endothelial cells; the medroxyprogesterone acetate which inhibits the production of plasminogen-activator by the endothelial cells [Nicosia, R. F. and Ottinetti, A., Lab. Invest. 63, 115 (1990)]; the fumagillin which inhibits the formation of tubules [Ingber, D. et al., Nature 348, 555 (1990)]; a polysaccharide sulfate (SD-4152) which inhibits the migration and multiplication of the endothelial cells; and the retinoic acid responsible for the differentiation and transformation of the endothelial cells [Tsutomu Oikawa, Kekkan to Naihi 2, 470 (1992)]. However, these substances did not work as angiogenesis-inhibitors in the clinical practice: some of them due to a strong side-effect and others due to an insufficient target effect.

The first, even clinically effective angiogenesis-inhibitor was the α-interferon [Bronty-Boye, D. and Zetter, B. E., Science 208, 516 (1980); Sidky, Y. A. and Borden, E. C., Cancer Res., 47, 5155 (1987)]. At present the clinical trials of several angiogenesis-inhibiting compounds with different chemical structures are under investigation; such compounds are for example the derivatives of fumagillin, e.g. the AGM-1470 [Kusaka, M. et al., Biophys. Res. Comm. 174, 1070 (1991)]; the 3-(2,4-dimethylpyrrol-5-yl)-indolin-2-one (SU-5416), U.S. Pat. No. 5,792,783; the 5-methylisoxazole-4-carboxylic-N-[4-(trifluoromethyl)-phenyl]-amide (leflunomide, SU-101), U.S. Pat. No. 5,610,173; the 2(R)-isobutyl-3(S)-dihydroxy-N-[2,2-dimethyl-1(S)—(N-methylcarbamoyl)-propyl]-succinamide (marimastat); the 3β-[{3-[(4-aminobutyl)-amino]-propyl}-amino]-5α-cholestane-7,24-diol-24-hydrogen sulfate (squalamine), U.S. Pat. No. 5,192,756; the ZD4190, an inhibitor of vascular endothelial growth factor etc.

Recently Japanese authors have described that the known borrelidin [chemically: 2'-(7-cyano-8,16-dihydroxy-9,11,13, 15-tetramethyl-18-oxo-oxacyclooctadeca-4,6-dien-2-yl)-cyclopentane-1'-carboxylic acid], which is a macroid antibiotic comprising a 18-membered ring [Keller-Schierlein, W., Experientia 22, 476 (1966); Helvetica Chim. Acta 50, 731 (1967); Anderson, B. F. et al., Aust. J. Chem. 42, 717 (1989)] has angiogenesis-inhibiting effect due to the property that it induces the apoptosis of the cells forming capillary tubules [Wakabayashi, T. et al., J. Antibiot. 50, 671 (1997)]. Furthermore, it has been proved that it is effective against cell lines WiDr of human colon cancer and PC-3 of human prostate cancer (published Japanese patent applications Nos. 8-173,167 and 9-227,549).

Furthermore, it is known that the borrelidin exerts antibacterial, antiviral, herbicidal and insecticidal effects and has a medium $LD_{50}$ value (Glasby, J. S., Encyclopedia of Antibiotics, p. 145, J. Wiley (editor), 1979).

It is known from the literature and it is supported even by our own investigations that the efficiency of borrelidin is directed towards two tumourbiological events: the proliferation on the one hand and the capillary formation by the endothelial cells, that is the angiogenesis, on the other hand. Although there is a difference in respect of the sensitivity of the two cellular functions (about a five fold difference exists in favour of capillary formation), this selectivity is yet of smaller degree when we consider the inhibition of cell proliferation aimed at other cell kinds.

The invention aims at separating the two cell-biological effects by modifying the structure of borrelidin. More specifically, the invention aims at preparing, by transforming the carboxyl group on the cyclopentane ring of the borrelidin molecule, novel borrelidin derivatives which exert a much stronger effect on the capillary formation by the endothelial cells than on the cell proliferation. Namely, according to our hypothesis, in the clinical practice an angiogenesis-inhibiting active agent is needed which inhibits the cell proliferation only in higher doses. (Here it is mentioned that the selectivity of the known angiogenesis-inhibiting compounds prevails in the fact that they inhibit the proliferation of endothelial cells more definitely than the division of the other cells of the organism.)

During our investigations it has been surprisingly observed that the novel borrelidin derivatives of general formula (I)

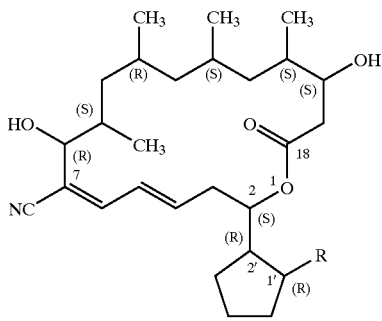

fully satisfy the above aims.

This recognition is surprising for a person skilled in the art because only a few borrelidin derivatives are known in the literature, i.e. its methyl ester and the diacetate of the methyl ester were prepared by Anderson, K. and Rickards, R. W. [Nature 206, 269 (1965)], further its benzyl ester and the bis-O-(4-nitrobenzoyl) derivative of the borrelidin methyl ester were described by Berger, J. et al. [Arch. Biochem. 22, 476 (1949)], and no any biological effect of these compounds was mentioned by the above authors. On the other hand, according to the literature only those borrelidin derivatives have angiogenesis inhibiting effect in which the carboxyl group located on the cyclopentane ring is not substituted. Such compounds are described for example in the published Japanese patent application JP 09227549-A (Kokai) which specifies compounds wherein a nitrile or carboxyl group is bonded to the carbon atom in position 7 of the borrelidin skeleton and a hydrogen atom or a lower alkyl group is bonded to the carbon atom in position 9.

Based on the above, the invention relates to compounds of general formula (I)—wherein R stands for a group of the general formula —$COOR^1$, —$CONR^2R^3$, —$CONR^4CONR^4R^5$ or —$CH_2OR^6$, wherein $R^1$ stands for a $C_{2-6}$ alkyl group; a $C_{1-6}$ alkyl group substituted by hydroxyl, amino, di($C_{1-4}$ alkyl)-amino group or 5–8-membered saturated, nitrogen-containing heterocyclic group (which may comprise beside the nitrogen atom even an oxygen atom or one or two further nitrogen atoms) or by 5- or 6-membered, nitrogen-containing aromatic heterocyclic group (which may comprise beside the nitrogen atom even an oxygen atom or one or two further nitrogen atoms); or a $C_{3-6}$ cycloalkyl group;

$R^2$ and $R^3$ are identical or different and stand independently from each other for hydrogen atom or a $C_{1-6}$ alkyl group which optionally may be substituted by halogen atom, hydroxyl, amino, $C_{2-5}$ alkoxycarbonyl, di($C_{1-4}$ alkyl)-amino group or 5–8-membered saturated, nitrogen-containing heterocyclic group (which may comprise beside the nitrogen atom even an oxygen atom or one or two further nitrogen atoms) or 5- or 6-membered aromatic homocyclic group or aromatic heterocyclic group containing an oxygen and/or nitrogen atom; a 5- or 6-membered cycloalkyl or a heteroaryl group;

$R^4$ and $R^5$ are identical or different and stand independently from each other for a hydrogen atom, a $C_{1-6}$ alkyl group, a $C_{3-6}$ cycloalkyl group or an optionally substituted phenyl group;

$R^6$ stands for a hydrogen atom; a $C_{1-5}$ alkyl, a $C_{3-6}$ cycloalkyl or a $C_{2-6}$ aliphatic acyl group which optionally may be substituted by halogen atom, amino, di($C_{1-4}$ alkyl)-amino or optionally substituted phenyl group; an optionally substituted carbamoyl group, an optionally substituted benzoyl group or a $C_{1-4}$ alkylsulfonyl group— and their tautomers, solvates, the mixtures thereof and the acid-addition salts of all these compounds.

Here it is mentioned that in the drawing of the general formula (I) the letters (R) and (S) designate the absolute configuration of the corresponding carbon atoms.

In the enumeration of the meanings of the substituents of the compounds of general formula (I) the designation "alkyl group" relates both to straight or branched chain groups. Such groups are for example the ethyl, propyl, isopropyl, butyl, isobutyl, sec-butyl, tert-butyl, pentyl, isopentyl, neopentyl, tert-pentyl, 1-ethyl-propyl, hexyl and isohexyl groups.

The cycloalkyl group can be cyclopropyl, cyclopentyl or cyclohexyl group.

The halogen atom can be chlorine or bromine atom.

In the meaning of $R^1$, $R^2$ and $R^3$ the 5–8-membered saturated, nitrogen-containing heterocyclic group can be for example but not exclusively 1-pyrrolidinyl, 1-piperidinyl, hexa-hydro-1H-azepin-1-yl, octahydroazocin-1-yl, piperazinyl and morpholinyl group.

In the meaning of $R^2$ and $R^3$ the $C_{2-5}$ alkoxycarbonyl group can be for example but not exclusively carbometoxymethyl, carbo-t-butyloxymethyl, carbomethoxyethyl and carbometoxypropyl group.

In the meaning of $R^2$ and $R^3$ the 5- or 6-membered aromatic homocyclic group can be for example but not exclusively phenyl or substituted phenyl group.

In the meaning of $R^1$, $R^2$ and $R^3$ the designations "5- or 6-membered aromatic heterocyclic group containing oxygen and/or nitrogen" and "heteroaryl group", resp., relate for example but not exclusively to the following groups: furyl, pyrrolyl, oxazolyl, isoxazolyl, imidazolyl, pyrazolyl, 1,2,3-oxadiazolyl, 1,2,4-oxadiazolyl, 1,3,4-oxadiazolyl, 1,2,3-triazolyl, 1,2,4-triazolyl, pyridazinyl, pyrimidinyl, pyrazinyl, 1,3,5-triazinyl, 2-pyridyl, 3-pyridyl and 4-pyridyl groups.

In the meaning of $R^6$ the designation "$C_{2-6}$ aliphatic acyl group" relates for example to acetyl, propionyl, butanoyl, isobutanoyl, sec-butanoyl, tert-butanoyl, n-caproyl or isocaproyl group. The term "$C_{1-4}$ alkylsulfonyl group relates for example to methanesulfonyl or ethanesulfonyl group. Furthermore, the term "optionally substituted carbamoyl group" relates to carbamoyl, $C_{1-6}$ alkylcarbamoyl, $C_{3-6}$ cycloalkylcarbamoyl or carbamoyl groups substituted by $C_{2-6}$ aliphatic acyl group, which optionally may be substituted by a halogen atom, like e.g. the chloroacetylcarbamoyl group.

Under the term "salts" formed with the compounds of general formula (I) the salts formed with physiologically acceptable inorganic and organic acids should be understood. Such acids suitable for salt-formation are e.g. the hydrochloric acid, the hydrobromic acid, the phosphoric acid or the sulfuric acid. For example formic acid, acetic acid, maleic acid, fumaric acid, succinic acid, lactic acid, citric acid or methanesulfonic acid can be used as organic acid.

An advantageous group of the compounds of general formula (I) according to the invention comprises compounds of general formula (I), wherein R stands for general formula —CONR²R³, wherein R² and R³ stand for hydrogen atom or one of R² and R³ stands for hydrogen atom and the other represents a $C_{1-6}$ alkyl group substituted by a 5- or 6-membered aromatic heterocyclic group containing a nitrogen atom.

For preparing the compounds of general formula (I) the esterifying, amidating and reducing, resp., methods can be used which are generally known from the literature, e.g. from the Synthetic Organic Chemistry (Wagner, R. B. and Zook, H. D., Wiley, N.Y., 1956).

The compounds of general formula (I) can be prepared by adapting the above general methods, for example by using the following processes:

a) reaction of an acid chloride formed from borrelidin with a suitable alcohol or amine,
b) direct esterification or amidation of borrelidin in the presence of carbodiimide and a base,
c) transesterification of an ester, formed from borrelidin, with a suitable alcohol,
d) reaction of borrelidin methyl ester with a suitable amine,
e) formation of an active ester from borrelidin e.g. with N-hydroxybenztriazole, then reaction with a suitable alcohol or amine,
f) formation of a mixed anhydride from borrelidin e.g. with chloroformic acid ester, then reaction with a suitable amine,
g) reduction of a mixed anhydride formed from borrelidin with a metal hydride to an alcohol,
h) alkylation and acylation, resp., of an alcohol prepared from borrelidin.

We have found that the novel ester derivatives of borrelidin according to the invention can be most preferably prepared by reacting an active derivative, formed from borrelidin with N-hydroxybenztriazole in the presence of carbodiimide, with a suitable alcohol.

The reaction is carried out in inert solvents, most preferably in tetrahydrofuran. In the process dicyclohexylcarbodiimide (DCC) is used as carbodiimide and dimethylaminopyridine (DMAP) is used as a base. It is suitable to use an excess of 10 moles from the alcohol component. The reaction is carried out at a temperature between 0° C. and 50° C., preferably at 20° C., under stirring during 1–8 hours, preferably during 3 hours.

The acid amide derivatives of borrelidin can be very preferably prepared for example with the mixed anhydride derivative formed with chloroformic acid ester. The reaction can be carried out in inert water-free solvents like e.g. tetrahydrofuran, dichloromethane, carbon tetrachloride. Triethyl amine, pyridine and dimethylaminopyridine can be used as acid-binding agent. From the amine to be coupled 1–10 moles can be used. The reaction is carried out by stirring at a temperature between −20° C. and +20° C., during 1–8 hours. In our most preferred process the mixed anhydride derivative is formed in water-free tetrahydrofuran at −20° C., in the presence of triethyl amine, with isobutyl chloroformate, then the reaction is carried out with 5 moles of amine during 3 hours.

The alcohol derivative of borrelidin can be prepared most preferably from a suitable mixed anhydride derivative of borrelidin by reduction carried out with an aqueous complex metal hydride, preferably sodium borohydride, in tetrahydrofuran at −20° C.

The alkylation and acylation, resp., of the alcohol derivative of borrelidin can be carried out in a way known per se.

It is evident for a person skilled in the art that when preparing compounds of general formula (I), which have starting compounds wherein certain substituents contain reactive group(s) not to be transformed in a given reaction, then this (these) group(s) can be protected in a manner known per se in the organic chemistry, and the protective group(s) are removed after the given reaction in such a way that other parts of the molecule should not undergo any undesired transformation. For protecting the said groups, usually employed protective groups known per se can be used. Such protective groups are known for example from the book "Protective Groups in Organic Synthesis" by Greene, T. W. and Wuts, P. (John Wiley & Sons, New York, 1991).

A part of the compounds of general formula (I) according to the invention contains a basic N atom which is suitable for forming salts. Such bases of general formula (I) can be transformed to—preferably pharmaceutically acceptable—acid-addition salts in a known way, for example by dissolving the base in a suitable organic solvent and adding the suitable acid or a solution of the acid, prepared with a suitable organic solvent. The thus-obtained salt is separated by filtration or by evaporating the solvent in vacuo and, if desired, it can be purified in a known way, for example by recrystallisation.

As mentioned above, the compounds of general formula (I) according to the invention have valuable biological efficiency, namely they show remarkable angiogenesis-inhibiting effect which is accompanied by a very favourable selectivity.

The angiogenesis-inhibiting effect of the compounds according to the invention has been determined by measuring the effect on the proliferation of and the capillary formation by the endothelial cells. The test methods are shown below.

Examination of Cell Proliferation

The endothelial cells ECV 304 (DSMZ No. ACC310) were propageted in an in vitro monolayer culture in a culture medium RPMI 1640 (SIGMA, USA) containing 10% fetal calf serum (Protein GMK, Gödöllö, Hungary). The borrelidin and its novel derivatives of general formula (I) according to the invention were added in the exponential period of the culture for attaining the different end concentrations (0.1–100 µg/ml). The growth of the cell culture was followed in a Fluoroscan Ascent FL apparatus on the basis of the change in the amount of the DNA, measured with the aid of the Hoechst 33342 stain.

Similar proliferation-inhibiting effect of borrelidin and the compounds according to the invention of general formula (I) on the endothelial proliferation could be observed even on a cell culture prepared from human umbilical cord (HUVEC).

Examination of Endothelial Capillary Formation

Basal membrane protein gel prepared from murine EHS tumor, which induces capillary formation, was put onto ECV 304 endothelial cells. The treatment with the borrelidin and the novel borrelidin derivatives of general formula (I) according to the invention was carried out in the same way as in case of the examination of cell proliferation. The extent by which the cells take part in the capillary formation was examined microscopically and by the aid of a morphometrical program, and the thus-obtained data were expressed in percent of the untreated control.

Results

The two methods proved to be suitable for demonstrating that the novel borrelidin derivatives according to the invention fulfil the requirement of selectively inhibiting the capillary formation. Namely, it has been stated that, relating to borrelidin, the cell-proliferation-inhibiting effect of the novel derivatives of general formula (I) definitely decreases whereas the capillary-formation-inhibiting effect changes only in a small degree or not at all. The relative degree of selectivity was determined for each compound by multiplying the ratios of the active agent concentrations that inhibit the cell proliferation in 50% and which inhibit the capillary formation. (The ratios were formed by dividing the suitable inhibiting concentration of the novel compound according to the invention by the suitable inhibiting concentration of borrelidin.) On the basis of the thus-calculated selectivity index the compound of Example 1 inhibits the capillary formation 60 times, the compound of Example 3 37 times, the compound of Example 2 7.5 times and the compound of Example 4 6 times better than the cell proliferation, in relation to the borrelidin.

The test data relating to the inhibition of formation of capillary tubules were confirmed when using the "microvessel formation" method [Parish et al., Cancer Res. 59, 3433 (1999)]. This method enabled us to study the neovascularization in a tissue culture formed from the artery of human placenta. We could state that the borrelidin derivatives according to the invention considerably inhibit the propagation of endothelial cells and even better the formation of tubules.

Based on our test results we could conclude to the fact that the novel borrelidin derivatives according to the invention act primarily on a cellular mechanism which is able to interrupt the capillarisation of endothelial cells and influences the proliferation of such cells only in a higher concentration. Our recognition that in the same endothelial cell culture the novel borrelidin derivatives according to the invention inhibit the tubule formation in a lower concentration than the proliferation of the endothelial cells, is not only novel but even surprising. Consequently, the selectivity does not appear in the dissimilar sensitivity of different cells but it can be observed between the intercellular connections, directing the capillary formation, and the cell proliferation.

Investigation into the Antitumorous Effect in Metastasis Model Systems

1. In a Lewis lung adenocarcinoma model [Holmgren et al., Nature Medicine 1, 149 (1995)] the borrelidin inhibited in a very small degree the propagation of metastatic nodules being formed after removing the primary tumour in lung. On the other hand, the compound according to Example 15 inhibited very considerably the increase of micrometastases not only with intraperitoneal but also with per os administration when adding one fifth of the toxic dose.

2. In a colon 38 spleen-liver model [Dong, Z. et al., J. Natl. Cancer Inst. 86, 913 (1994); Shaheen, R. M. et al., Cancer Research 89, 5412 (1999)] test system the metastasis-forming ability of mouse colon adenocarcinoma cells transplanted into the spleen considerably decreased after the subtoxic administration of the compound of Example 15.

The compounds according to the invention can be used for therapeutical purposes either alone or preferably in the form of pharmaceutical compositions. Such compositions fall under the scope of the present invention.

These pharmaceutical compositions contain a compound of general formula (I) in an amount necessary for exerting the desired effect, together with carriers, fillers, diluents and/or other pharmaceutical auxiliary materials known per se and generally used in the pharmaceutical industry.

For example water, alcohols, gelatine, lactose, saccharose, starch, pectin, magnesium stearate, stearic acid, talc, various animal or plant oils as well as glycols, such as propyleneglycol or polyethylenglycol, can be used as carriers, diluents and fillers mentioned above. As pharmaceutical auxiliary materials e.g. preservatives, antioxidants, different natural or synthetic emulsifying, dispersing or wetting agents, colouring agents, flavouring agents, buffering agents, disintegrating agents and other materials enhancing the biological utilization of the active agent can be used.

The pharmaceutical compositions according to the invention may be in the usual forms, such as oral preparations which can be prepared by using the above-mentioned pharmaceutical auxiliary agents. These oral compositions may be solid pharmaceutical forms such as tablets, capsules, powders, pills, dragées or granules, or liquid pharmaceutical forms such as syrups, solutions, emulsions or suspensions. The rectal preparations can be suppositories. The parenteral preparations, that are administered by avoiding the gastric system, may be for example injection or infusion solutions. Further, the pharmaceutical compositions according to the invention can be external preparations such as ointments, creams, water for compresses, eye-rinsing solutions, eye-drops etc.

Although the dose of the compounds according to the invention necessary for exerting the required pharmaceutical effect depends inter alia on the individual state and age of the patient and is finally determined by the doctor, for preventing and/or treating diseases, wherein the inhibition of angiogenesis appearing in connection with the disease is requested, a dose between about 0.5 mg and about 100 mg per 1 kg of body weight can be used. This dose can be administered daily in several portions, considering even the conditions of absorption.

The pharmaceutical compositions comprising compounds of general formula (I) according to the invention can be used beside surgical intervention and radiotherapy as adjuvants primarily for treating and preventing the increase of tumours and for limiting the formation of cancer metastases. Besides, they can be used for treating other diseases and states where the inhibition, control and/or regression of vascularisation exerts a favourable effect; here we mention as examples the arthritis, various ophthalmological cases (e.g. subretinalis neovascularisatio) as well as psoriasis.

Based on the above, the present invention also provides a method of treating angiogenic diseases in mammals; caused by excessive inappropriate angiogenesis, which comprises administering to a mammal in need of such treatment an effective dosage of a compound of general formula (I).

The compounds according to the invention and the process for their preparation are further illustrated by the following non-limiting examples.

EXAMPLE 1

Borrelidin-2-morpholinoethyl ester [(I), R=COO$(CH_2)_2$—$C_4H_8NO$]

120 mg (0.245 mmol) of borrelidin were dissolved at 20° C. while stirring in 5 ml of abs. tetrahydrofuran, then 38 mg (0.245 mmol) of 1-hydroxybenztriazole, 30 mg (0.245 mmol) of dimethyl-aminopyridine and 65 mg (0.31 mmol) of dicyclohexyl carbodiimide were added to the solution. After stirring for 30 minutes, 0.3 ml (0.32 g, 2.45 mmol) of 4-(2-hydroxyethyl)-morpholine was added. After stirring for 3 hours at 20° C., the starting compound ($R_f$=0.43) disappeared and the product (Rf=0.51) appeared, which was proved by thin-layer chromatography (silica gel plate, eluent system: chloroform/methanol 95:5). The reaction mixture was evaporated to dryness. The dry residue was dissolved in 50 ml of chloroform, washed with 2×50 ml of water, dried over sodium sulfate and evaporated to dryness. The dry residue was chromatographed on a silica gel column with mixtures of chloroform and ethyl acetate of increasing ethyl acetate content. The fractions containing the product eluting with a 65:35 eluting mixture were combined and evaporated to dryness. The structure of the thus-obtained oily product (133 mg) was confirmed by spectroscopic (PMR, CMR, TS) data.

(It is mentioned that the designations 1", 2", 3", 5" and 6" in the spectral data relate to the morpholine ring.)

Characteristic Spectral Data $^1$H-NMR (CDCl$_3$; δ [ppm], δ$_{TMS}$=0; multiplicity): H-2: 4.93, d,t; H-4: 6.20 ddd; H-5: 6.36, dd; H-6: 6.82, d; H-8: 4.10; H-16: 3.84, m; —O—CH$_2$—CH$_2$—: 4.12, m and 4.30, m; —CH$_2$—CH$_2$-1": ~2.50; H$_2$-2" and H$_2$-6": ~2.50; H$_2$-3" and H$_2$-5": 3.68, t.

$^{13}$C-NMR (CDCl$_3$; δ [ppm], δ$_{TMS}$=0; multiplicity): C-2: 76.4, d; C-4: 138.5, d; C-5: 126.9, d; C-6: 143.9, d; C-7: 116.0, s; 7-CN: 118.2, s; C-8: 73.1, d; C-16: 70.0, d; C-18: 172.4, s; 1'-CO—O: 176.0, s; O—CH$_2$—CH$_2$: 61.8, t; CH$_2$—CH$_2$-1": 57.0, t; C-2", 6": 53.8, t; C-3", 5": 66.9, d.

TS (El, 70 eV; m/z): 602, [M]$^+$·; 113, [CH$_2$=CH-morpholinyl]$^+$·; 100, [CH$_2$=morpholinyl]$^+$·.

EXAMPLE 2

Borrelidin-2-(2-pyridyl)-ethyl ester [(I), R=COO(CH$_2$)$_2$—C$_5$H$_4$N]

To 1-hydroxybenztriazole active ester, prepared from 150 mg (0.306 mmol) of borrelidin according to Example 1, 0.35 ml (0.38 g, 3.06 mmol) of 2-(2-hydroxyethyl)-pyridine was added. After stirring for 3 hours at 20° C., the starting borrelidin (R$_f$=0.43) disappeared and the product (R$_f$=0.58) appeared, which was proved by thin-layer chromatography (silica gel plate, eluent system: chloroform/methanol 95:5). The reaction mixture was evaporated to dryness. The dry residue was dissolved in 100 ml of chloroform, washed with 3×30 ml of water, dried over sodium sulfate and evaporated to dryness. The dry residue was chromatographed on a silica gel column with mixtures of chloroform and ethyl acetate of increasing ethyl acetate content. The fractions containing the product eluting with a 1:1 eluting mixture were combined and evaporated to dryness. The structure of the thus-obtained solidifying oily product (171 mg) was confirmed by spectroscopic (PMR, CMR, TS) data.

(It is mentioned that the designations 2", 3", 4", 5" and 6" in the spectral data relate to the pyridine ring.)

Characteristic Spectral Data $^1$H-NMR (CDCl$_3$; δ [ppm], δ$_{TMS}$=0; multiplicity): H-2: 4.90, d,t; H-4: 6.15 ddd; H-5: 6.36, dd; H-6: 6.80, d; H-8: 4.12; H-16: 3.85, m; —O—CH$_2$—CH$_2$—: 4.35–4.60, m; —CH$_2$—CH$_2$-2": 3.10, t; H-3": 7.17, d; H-4": 7.62, m; H-5": 7.15, m; H-6": 6.52, d.

$^{13}$C-NMR (CDCl$_3$; δ [ppm], δ$_{TMS}$=0; multiplicity): C-2: 76.2, d; C-4: 138.6, d; C-5: 126.8, d; C-6: 144.0, d; C-7: 115.9, s; 7-CN: 118.2, s; C-8: 73.1, d; C-16: 70.1, d; C-18: 172.4, s; 1'-CO—O—: 176.0, s; —O—CH$_2$—CH$_2$—: 63.8, t; —CH$_2$—CH$_2$-2": 37.3, t; C-2": 157.9, s; C-3": 123.3, d; C-4": 136.4, d; C-5": 126.9, d; C-6":149.4, d.

TS (El, 70 eV; m/z): 594, [M]$^+$·.

EXAMPLE 3

Borrelidin amide [(I), R=CONH$_2$]

150 mg (0.306 mmol) of borrelidin were dissolved in 10 ml of abs. tetrahydrofuran while stirring, then 47 μl (0.33 mmol) of triethyl amine and 44 μl (0.33 mmol) of isobutyl chloroformate were added at −20° C. After stirring for 30 minutes at −20° C. the triethyl amine.HCl salt was filtered out and 100 μl (1.5 mmol) of a 25% aqueous ammonium hydroxide solution were added to the solution. After stirring the reaction mixture for 3 hours, the starting borrelidin (R$_f$=0.43) disappeared and the product (R$_f$=0.33) appeared, which was proved by thin-layer chromatography (silica gel plate, eluent system: chloroform/methanol 95:5). The pH of the reaction mixture was set to 7 with 1–2 drops of acetic acid, then the reaction mixture was evaporated to dryness. The dry residue was dissolved in 100 ml of chloroform, washed with 2×30 ml of water, dried over sodium sulfate and evaporated to dryness. The dry residue was chromatographed on a silica gel column with mixtures of chloroform and ethyl acetate of increasing ethyl acetate content. The fractions containing the product eluting with a 55:45 eluting mixture were combined and evaporated to dryness. The structure of the thus-obtained solidifying oily product (109 mg) was confirmed by spectroscopic (PMR, CMR, TS) data.

Characteristic Spectral Data $^1$H-NMR (CDCl$_3$; δ [ppm], δ$_{TMS}$=0; multiplicity): H-2: 4.90, d,t; H-4: 6.16 ddd; H-5: 6.30, dd; H-6: 6.75, d; H-8: 4.04; 8-OH: 2.95; H-16: 3.75, m; NH$_2$: 5.55 és 5.72.

$^{13}$C-NMR (CDCl$_3$; δ [ppm], δ$_{TMS}$=0; multiplicity): C-2: 76.6, d; C-4: 138.8, d; C-5: 126.8, d; C-6: 144.0, d; C-7: 115.9, s; 7-CN: 118.3, s; C-8: 73.0, d; C-16: 69.8, d; C-18: 172.4, s; 1'-CONH$_2$: 178.1, s.

TS (El, 70 eV; m/z): 488, [M] ]$^+$·; 470, [M—H$_2$O] ]$^+$·; 452, [M—2H$_2$O] ]$^+$·; 435, [M—H$_2$O—NH$_3$] ]$^+$·; 417, [M—2H$_2$O—NH$_3$] ]$^+$·.

TS (Cl, i-butane; m/z): 489, [M+H] ]$^+$; 471, [M—H—H$_2$O] ]$^+$.

EXAMPLE 4

Borrelidin 2-morpholinoethyl amide [(I), R=CONH(CH$_2$)$_2$—C$_4$H$_8$NO]

To a mixed anhydride solution prepared according to Example 3 from 150 mg (0.306 mmol) of borrelidin 0.25 ml (1.9 mmol, 0.25 g) of 4-(2-aminoethyl)-morpholine was added. After stirring for 3 hours, the starting borrelidin (R$_f$=0.43) disappeared and the product (R$_f$=0.22) appeared, which was proved by thin-layer chromatography (silica gel plate, eluent system: chloroform/methanol 95:5). The reaction mixture was evaporated to drynesss. The dry residue was dissolved in 100 ml of chloroform, washed with 3×30 ml of water, dried over sodium sulfate and evaporated to dryness. The dry residue was chromatographed on a silica gel column with mixtures of chloroform and ethyl acetate of increasing ethyl acetate content. The fractions containing the product eluting with a 95:5 eluting mixture were combined and evaporated to dryness. The structure of the thus-obtained solidifying oily product (172 mg) was confirmed by spectroscopic (PMR, CMR, TS) data.

(It is mentioned that the designations 2", 3", 5" and 6" in the spectral data relate to the morpholine ring.)

Characteristic Spectral Data $^1$H-NMR (CDCl$_3$; δ [ppm], δ$_{TMS}$=0; multiplicity): H-2: 5.00, d,t; H-4: 6.20 ddd; H-5: 6.35, dd; H-6: 6.80, d; H-8: 4.10; H-16: 3.82, m; NH: 6.15, t; NH—CH$_2$—CH$_2$—N: 3.20–3.45, m; NH—CH$_2$—CH$_2$—N: 2.32, m; H-2"-6": 2.45, m; H-3"-5": 3.70, m.

$^{13}$C-NMR (CDCl$_3$; δ [ppm], δ$_{TMS}$=0; multiplicity): C-2: 76.5, d; C-4: 139.1, d; C-5: 126.5, d; C-6: 144.1, d; C-7: 115.8, s; 7-CN: 118.3, s; C-8: 73.1, d; C-16: 69.2, d; C-18:

172.2, s; 1'-CO—N: 175.5, s; NH—CH$_2$—CH$_2$—N: 57.1, t és 36.3, t; C-2", 6": 53.3, t; C-3", 5": 66.8 t.

TS (EI, 70 eV; m/z): 601, [M] ]$^{+\cdot}$; 585, [M—H$_2$O] ]$^{+\cdot}$; 113, [CH$_2$=CH-morpholinyl] ]$^+$; 100, [CH$_2$=morpholinyl] ]$^+$.

EXAMPLE 5

Borrelidin-alcohol [(I), R$_1$=CH$_2$OH]

A mixed anhydride solution prepared from 150 mg (0.306 mmol) of borrelidin according to Example 3 was dropped to the solution of 60 mg (1.5 mmol) of NaBH$_4$ in 2 ml of water and cooled to −20° C. After stirring for 5 hours, the starting borrelidin (R$_f$=0.43) disappeared and the product (R$_f$=0.52) appeared, which was proved by thin-layer chromatography (silica gel plate, eluent system: chloroform/methanol 95:5). Thereafter 1–2 drops of acetic acid were added to the reaction mixture for decomposing the excess of NaBH$_4$, then the reaction mixture was evaporated to dryness. The dry residue was dissolved in 100 ml of chloroform, washed with 2×30 ml of water, dried over sodium sulfate and evaporated to dryness. The dry residue (185 mg) was chromatographed on a silica gel column with mixtures of chloroform and ethyl acetate of increasing ethyl acetate content. The fractions containing the product eluting with a 3:1 eluting mixture were combined and evaporated to dryness. The structure of the thus-obtained solidifying oily product (117 mg) was confirmed by spectroscopic (PMR, CMR, TS) data.

Characteristic Spectral Data $^1$H-NMR (CDCl$_3$; δ [ppm], δ$_{TMS}$=0; multiplicity): H-2: 4.92, d,t; H-4: 6.20 ddd; H-5: 6.35, dd; H-6: 6.80, d; H-8: 4.10; H-16: 3.87, m; 1'-CH$_2$—OH: 3.45, m.

$^{13}$C-NMR (CDCl$_3$; δ [ppm], δ$_{TMS}$=0; multiplicity): C-2: 76.7, d; C-4: 139.1, d; C-5: 126.7, d; C-6: 144.1, d; C-7: 115.8, s; 7-CN: 118.3, s; C-8: 73.0, d; C-16: 70.5, d; C-18: 172.3, s; 1'-CH$_2$—OH: 66.4, t.

TS (EI, 70 eV; m/z): 475, [M] ]$^{+\cdot}$; 457, [M—H$_2$O] ]$^{+\cdot}$; 439, [M—2H$_2$O] ]$^{+\cdot}$.

TS (CI, i-butane; m/z): 476, [M+H] ]$^+$; 458, [M+H—H$_2$O] ]$^+$; 440, [M+H—2H$_2$O] ]$^+$.

EXAMPLE 6

Borrelidin-N,N'-dicyclohexylcarbamidoamide [(I), R=CON(C$_6$H$_{11}$)CONHC$_6$H$_{11}$]

98 mg (0.2 mmol) of borrelidin were dissolved at 20° C. in 2 ml of abs. tetrahydrofuran while stirring, then 124 mg (0.6 mmol) of dicyclohexylcarbodiimide were added to the solution. The reaction mixture was stirred at the same temperature, and the progress of the reaction was followed by thin-layer chromatography. On a silica gel plate, in a chloroform/methanol 95:5 eluting system, the starting borrelidin (R$_f$=0.43) disappeared after 5 hours and the product (R$_f$=0.74) appeared. Thereafter the reaction mixture was evaporated to dryness and the raw product (240 mg) was chromatographed on a silica gel column with mixtures of chloroform and ethyl acetate of increasing ethyl acetate content. The fractions containing the product eluting with a 8:2 eluting mixture were combined and evaporated to dryness. The structure of the thus-obtained solidifying oily product (105 mg) was confirmed by spectroscopic (PMR, CMR, TS) data.

Characteristic Spectral Data $^1$H-NMR (CDCl$_3$; δ [ppm], δ$_{TMS}$=0; multiplicity): H-2: 4.93, d, t; H-4: 6.28 ddd; H-5: 6.36, dd; H-6: 6.84, d; H-8: ~4.10; H-16: 3.85, m; cyclohexyl groups: 3.65, m, 1H; 4.05, m, 1H; 1.4–2.1, m, 20H.

$^{13}$C-NMR (CDCl$_3$; δ [ppm], δ$_{TMS}$=0; multiplicity): C-2: 77.0, d; C-4: 139.0, d; C-5: 126.7, d; C-6: 144.1, d; C-7: 115.7, s; 7-CN: 118.2, s; C-8: 73.1, d; C-16: 69.1, d; C-18: 172.7, s; 1'-CO—N: broadening sign, not emerging from the basic line; N—CO—N: 153.6, s; cyclohexyl groups: 50.1, d; 40.9, d (broadening sign); 32.7, t (2C); 32.6, t (2C); 24.7, t; 25.9, t (2C); 26.0, t (2C).

TS (EI, 70 eV; m/z): 695, [M]$^{+\cdot}$; 570, [M—O=C=N—C$_6$H$_{11}$]$^{+\cdot}$; 552, [570—H$_2$O]$^{+\cdot}$.

TS (CI, i-butane; m/z): 696, [M+H]$^{+\cdot}$; 571, [M+H—O=C=N—C$_6$H$_{11}$]$^+$; 553, [571—H$_2$O]$^+$; 83, [C$_6$H$_{11}$]$^+$.

EXAMPLE 7

Borrelidin-benzylamide [(I), R=CONHCH$_2$—C$_6$H$_5$]

To a mixed anhydride solution prepared from 200 mg (0.41 mmol) of borrelidin according to Example 3 220 μl (2 mmol, 2.14 mg) of benzylamine were added. After stirring for 3 hours, the starting borrelidin (R$_f$=0.52) disappeared and the product (R$_f$=0.69) appeared, which was proved by thin-layer chromatography (silica gel plate, eluent system: chloroform/methanol 3:7). The reaction mixture was evaporated to dryness. The dry residue was dissolved in 100 ml of chloroform, washed with 3×30 ml of water, dried over sodium sulfate and evaporated to dryness. The dry residue was chromatographed on a silica gel column with mixtures of chloroform and ethyl acetate of increasing ethyl acetate content. The fractions containing the product eluting with a 8:2 eluting mixture were combined and evaporated to dryness. The structure of the thus-obtained solidifying oily product (135 mg) was confirmed by spectroscopic (PMR, CMR, TS) data.

Characteristic Spectral Data $^1$H-NMR (CDCl$_3$; δ [ppm], δ$_{TMS}$=0; multiplicy): H-2: 4.95, d,t; H-4: 6.24, ddd; H-5: 6.35, dd; H-6: 6.79, d; H-8: 4.10, m; H-16: 3.80, m; 1'-CONH-5.98, t; NH—CH$_2$-Ph: 4.26, dd, and 4.44, dd; Ph: 7.15–7.35, m, 5H $^{13}$C-NMR (CDCl$_3$; δ [ppm], δ$_{TMS}$=0; multiplicity): C-2: 76.7, d; C-4: 138.8, d; C-5: 126.7, d; C-6: 144.0, d; C-7: 115.8, s; 7-CN: 118.3, s; C-8: 73.0, d; C-16: 69.8, d; C-18: 172.4, s; 1'-CO—NH—: 175.4, s; NH—CH$_2$-Ph: 43.8, t; Ph: 138.2, s; 128.7, d; 127.7, d; 127.6, d TS (EI, 70 eV; m/z): 578, [M]$^{+\cdot}$; 560, [M—H$_2$O]$^{+\cdot}$; 542, [M—2H$_2$O]$^{+\cdot}$; 435, [M—2H$_2$O—C$_6$H$_5$CH$_2$NH$_2$]$^{+\cdot}$; 106, [C$_7$H$_8$N]$^+$; 91, [C$_7$H$_7$]$^+$.

TS (CI, i-butane; m/z): 579, [M+H]$^+$; 561, [M+H—H$_2$O]$^+$; 106, C$_7$H$_8$N]$^+$; 91, [C$_7$H$_7$]$^+$.

EXAMPLE 8

Borrelidin-2-picolylamide [(I), R=CONHCH$_2$—C$_5$H$_4$N]

To a mixed anhydride solution prepared from 200 mg (0.41 mmol) of borrelidin according to Example 3 206 μl (2 mmol, 216 mg) of 2-picolylamine were added. After stirring for 3 hours, the starting borrelidin (R$_f$=0.52) disappeared and the product (R$_f$=0.29) appeared, which was proved by thin-layer chromatography (silica gel plate, eluent system: chloroform/methanol 3:7). The reaction mixture was evaporated to dryness. The dry residue was dissolved in 100 ml of chloroform, washed with 3×30 ml of water, dried over sodium sulfate and evaporated to dryness. The dry residue was chromatographed on a silica gel column with mixtures of chloroform and ethyl acetate of increasing ethyl acetate content. The fractions containing the product eluting with a 1:1 eluting mixture were combined and evaporated to dryness. The structure of the thus-obtained solidifying oily product (188 mg) was confirmed by spectroscopic (PMR, CMR, TS) data.

Characteristic Spectral Data $^1$H-NMR (CDCl$_3$; δ [ppm], δ$_{TMS}$=0; multiplicity): H-2: 5.00, dt; H-4: 6.20, ddd; H-5: 6.40, dd; H-6: 6.80, d; H-8: 4.15, m; H-16: 3.82, m; 1'-CONH—: 7.14, t; NH—CH$_2$-2Py: 4.55, d; Py: 7.20–7.36, m, 2H; 7.70, td, 1H and 8.50, d, 1H $^{13}$C-NMR (CDCl$_3$; δ [ppm], δ$_{TMS}$=0; multiplicity): C-2: 76.7, d; C-4: 139.2, d; C-5: 126.5, d; C-6: 144.2, d; C-7: 115.7, s; 7-CN: 118.2, s; C-8: 73.1, d; C-16: 69.3, d; C-18: 172.3, s; 1'-CO—NH—: 175.6, s; NH—CH$_2$-2Py: 44.3, t; Py: 156.3, s; 122.8, d; 137.2, d; 122.5, d; 148.8, d TS (EI, 70 eV; m/z): 579, [M]$^{+\cdot}$; 561, [M—H$_2$O]$^{+\cdot}$; 336, [C$_{20}$H$_{22}$N$_3$O$_2$]$^+$; 109, [C$_5$H$_4$NCH$_2$NH$_3$]$^+$; 107, [C$_6$H$_7$N$_2$]$^+$; 92, [C$_6$H$_6$N]$^+$.

TS (Cl, i-butane; m/z): 580, [M+H]$^+$.

EXAMPLE 9

Borrelidin-4-picolylamide [(I), R=CONHCH$_2$—C$_5$H$_4$N]

To a mixed anhydride solution prepared from 200 mg (0.41 mmol) of borrelidin according to Example 3 206 μl (2 mmol, 216 mg) of 4-pycolylamine were added. After stirring for 3 hours, the starting borrelidin (R$_f$=0.43) disappeared and the product (R$_f$=0.24) appeared, which was proved by thin-layer chromatography (silica gel plate, eluent system: chloroform/methanol 95:5). The reaction mixture was evaporated to dryness. The dry residue was dissolved in 100 ml of chloroform, washed with 3×30 ml of water, dried over sodium sulfate and evaporated to dryness. The dry residue was chromatographed on a silica gel column with mixtures of dichloromethane and ethyl acetate of increasing ethyl acetate content. The fractions containing the product eluting with a 15:85 eluting mixture were combined and evaporated to dryness. The structure of the thus-obtained solidifying oily product (201 mg) was confirmed by spectroscopic (PMR, CMR, TS) data.

Characteristic Spectral Data $^1$H-NMR (CDCl$_3$; δ [ppm], δ$_{TMS}$=0; multiplicity): H-2: 4.98, dt; H-4: 6.22, m; H-5: 6.36, dd; H-6: 6.78, d; H-8: 4.10, m; H-16: 3.78, m; 1'-CONH—: 6.55, t; NH—CH$_2$-4Py: 4.18, dd and 4.62, dd; Py: 7.15, d, 2H and 8.48, d, 2H $^{13}$C-NMR (CDCl$_3$; δ [ppm], δ$_{TMS}$=0; multiplicity): C-2: 76.6, d; C-4: 138.7, d; C-5: 126.7, d; C-6: 143.9, d; C-7: 116.0, s; 7-CN: 118.4, s; C-8: 72.9, d; C-16: 69.5, d; C-18: 172.2, s; 1'-CO—NH—: 176.0, s; NH—CH$_2$-4Py: 42.3, t; Py: 149.7, d; 122.2, d and 147.7, s TS (EI, 70 eV; m/z): 579, [M]$^{+\cdot}$; 561, [M—H$_2$O]$^{+\cdot}$; 336, [C$_{20}$H$_{22}$N$_3$O$_2$]$^+$, 107, [C$_6$H$_7$N$_2$]$^+$; 93 [C$_6$H$_7$N]$^+$; 92, C$_6$H$_6$N]$^+$.

TS (Cl, i-butane; m/z): 580, [M+H]$^+$; 562, [M+H—$_2$O]$^+$.

EXAMPLE 10

Borrelidin-2-furfurylamide [(I), R=CONHCH$_2$—C$_4$H$_3$O]

To a mixed anhydride solution prepared from 200 mg (0.41 mmol) of borrelidin according to Example 3 177 μl (2 mmol, 194 mg) of 2-furfurylamine were added. After stirring for 3 hours, the starting borrelidin (R$_f$=0.52) disappeared and the product (R. =0.70) appeared, which was proved by thin-layer chromatography (silica gel plate, eluent system: chloroform/ethyl acetate 3:7). The reaction mixture was evaporated to dryness. The dry residue was dissolved in 100 ml of chloroform, washed with 3×30 ml of water, dried over sodium sulfate and evaporated to dryness. The dry residue was chromatographed on a silica gel column with mixtures of dichloromethane and ethyl acetate of increasing ethyl acetate content. The fractions containing the product eluting with a 65:35 eluting mixture were combined and evaporated to dryness. The structure of the thus-obtained solidifying oily product (105 mg) was confirmed by spectroscopic (PMR, CMR, TS) data.

Characteristic Spectral Data

IR: 3357; 2958; 2213; 1723; 1651 cm$^{-1}$ $^1$H-NMR (CDCl$_3$; δ [ppm], δ$_{TMS}$=0; multiplicity): H-2: 4.88, dt; H-4: ~6.15, m; H-5: 6.30, dd; H-6: 6.75, d; H-8: 4.03, m; H-16: 3.76, m; 1'-CONH—: 5.86, t; NH—CH$_2$-2Fu: 4.28, dd and 4.48, dd; Fu: 6.13, dd; 6.25, d and 7.27, d $^{13}$C-NMR (CDCl$_3$; δ [ppm], δ$_{TMS}$=0; multiplicity): C-2: 76.7, d; C-4: 138.8, d; C-5: 126.7, d; C-6: 144.1, d; C-7: 115.7, s; 7-CN: 118.2, s; C-8: 73.1, d; C-16: 69.6, d; C-18: 172.5, s; 1'-CO—NH—: 175.2, s; NH—CH$_2$-2Fu: 36.8, t; Fu: 151.0, s; 110.5, d; 107.5, d; 142.2, d TS (EI, 70 eV; m/z): 568, [M]$^{+\cdot}$; 550, [M—H$_2$O]$^+$; 96, [C$_5$H$_6$NO]$^+$; 81, [C$_5$H$_5$O]$^+$.

TS (Cl, i-butane; m/z): 569, [M+H]$^+$; 551, [M+H—H$_2$O]$^+$; 96, C$_5$H$_6$NO]$^+$; 81, [C$_5$H$_5$O]$^+$.

EXAMPLE 11

Borrelidin-3-pyridylamide [(I), R=CONH—C$_5$H$_4$N]

To a mixed anhydride solution prepared from 200 mg (0.41 mmol) of borrelidin according to Example 3 188 mg (2 mmol) of 3-aminopyridin were added. After stirring for 3 hours, the starting borrelidin (R$_f$=0.43) disappeared and the product (R$_f$=0.25) appeared, which was proved by thin-layer chromatography (silica gel plate, eluent system: chloroform/methanol 95:5). The reaction mixture was evaporated to dryness. The dry residue was dissolved in 100 ml of chloroform, washed with 3×30 ml of water, dried over sodium sulfate and evaporated to dryness. The dry residue was chromatographed on a silica gel column with mixtures of dichloromethane and ethyl acetate of increasing ethyl acetate content. The fractions containing the product eluting with a 1:9 eluting mixture were combined and evaporated to dryness. The structure of the thus-obtained solidifying oily product (144 mg) was confirmed by spectroscopic (PMR, CMR, TS) data.

Characteristic Spectral Data

IR: 3318; 2958; 2212; 1730; 1542 cm$^{-1}$ $^1$H-NMR (CDCl$_3$; δ [ppm], δ$_{TMS}$=0; multiplicity): H-2: 4.92, dt; H-4: 6.20, m; H-5: 6.35, dd; H-6: 6.76, d; H-8: 4.08, d; H-16: 3.76, m; CO—NH-3Py: 7.70, s; Py: 8.53, d; 8.22-8-36, m, 2H and 7.25, t $^{13}$C-NMR (CDCl$_3$; δ [ppm], δ$_{TMS}$=0; multiplicity): C-2: 76.5, d; C-4: 138.5, d; C-5: 126.9, d; C-6: 143.9, d; C-7: 115.9, s; 7-CN: 118.2, s; C-8: 73.1, d; C-16: 70.6, d; C-18: 172.4, s; 1'-CO—NH—: 174.6, s; Py: 145.1, d; 126.9, s; 140.6, d; 123.7, d; 135.1, d TS (EI, 70 eV; m/z): 565, [M]$^{+\cdot}$; 547, [M—H$_2$O]$^{+\cdot}$; 322, [C$_{20}$H$_{22}$N$_3$O$_2$]$^+$; 121, [C$_6$H$_5$N$_2$O]$^+$; 95 [C$_5$H$_7$N$_2$]$^+$.

TS (Cl, i-butane; m/z): 566, [M+H]$^+$; 548, [M+H—H$_2$O]$^+$; 95 [C$_5$H$_7$N$_2$]$^+$.

EXAMPLE 12

Borrelidinyl-glycine-tert-butyl ester [(I), R=CONHCH$_2$—COOC$_4$H$_9$]

To a mixed anhydride solution prepared from 200 mg (0.41 mmol) of borrelidin according to Example 3 280 mg (1,67 mmol) of glycine-tert-butyl ester hydrochloride and 235 μl (1.69 mmol, 170 mg) of triethyl amine were added. After stirring for 3 hours, the starting borrelidin ($R_f$=0.52) disappeared and the product ($R_f$=0.73) appeared, which was proved by thin-layer chromatography (silica gel plate, eluent system: chloroform/ethyl acetate 3:7). The reaction mixture was evaporated to dryness. The dry residue was dissolved in 100 ml of chloroform, washed with 3×30 ml of water, dried over sodium sulfate and evaporated to dryness. The dry residue was chromatographed on a silica gel column with mixtures of chloroform and methanol of increasing methanol content. The fractions containing the product eluting with a 96:4 eluting mixture were combined and evaporated to dryness. The structure of the thus-obtained solidifying oily product (129 mg) was confirmed by spectroscopic (PMR, CMR, TS) data.

Characteristic Spectral Data $^1$H-NMR (CDCl$_3$; δ [ppm], $δ_{TMS}$=0; multiplicity): H-2: 4.92, dt; H-4: 6.22, m; H-5: 6.38, dd; H-6: 6.82, d; H-8: 4.10, dd; H-16: 3.85, m; CO—NH—CH$_2$: 6.15, t; NH—CH$_2$—CO—: 3.88, dd and 3.99, dd; tBu: 1.48, s, 3H $^{13}$C-NMR (CDCl$_3$; δ [ppm], $δ_{TMS}$=0; multiplicity): C-2: 76.7, d; C-4: 139.0, d; C-5: 126.7, d; C-6: 144.2, d; C-7: 115.7, s; 7-CN: 118.2, s; C-8: 73.1, d; C-16: 69.5, d; C-18: 172.5, s; 1'-CO—NH—: 175.5, s; NH—CH$_2$—CO: 42.2, t; CH$_2$—CO—O: 169.5, s; O—C—(CH$_3$)$_3$: 82.5, s; O—C—(CH$_3$)$_3$: 28.0, q TS (EI, 70 eV; m/z): 602, [M]$^{+ \cdot}$; 528, [M—C$_4$H$_9$OH]$^{+ \cdot}$; 435, [M—2H$_2$O—C$_5$H$_{13}$NO$_2$]$^{+ \cdot}$.

TS (CI, i-butane; m/z): 603, [M+H]$^+$; 547, [M+H—$_4$H$_8$]$^+$; 529, (M+H—C$_4$H$_9$OH]$^+$.

EXAMPLE 13

Borrelidin-cyclohexylamide [(I), R=CONH—C$_6$H$_{11}$]

To a mixed anhydride solution prepared from 200 mg (0.41 mmol) of borrelidin according to Example 3 234 μl (2 mmol, 203 mg) of cyclohexylamine were added. After stirring for 3 hours, the starting borrelidin ($R_f$=0.52) disappeared and the product ($R_f$=0.68) appeared, which was proved by thin-layer chromatography (silica gel plate, eluent system: chloroform/ethyl acetate 3:7). The reaction mixture was evaporated to dryness. The dry residue was dissolved in 100 ml of chloroform, washed with 3×30 ml of water, dried over sodium sulfate and evaporated to dryness. The dry residue was chromatographed on a silica gel column with mixtures of chloroform and methanol of increasing methanol content. The fractions containing the product eluting with a 96:4 eluting mixture were combined and evaporated to dryness. The structure of the thus-obtained solidifying oily product (205 mg) was confirmed by spectroscopic (PMR, CMR, TS) data.

Characteristic Spectral Data

IR: 3344; 2931; 2213; 1717; 1647; 1541 cm$^{-1}$ $^1$H-NMR (CDCl$_3$; δ [ppm], $δ_{TMS}$=0; multiplicity): H-2: 4.94, dt; H-4: 6.25, m; H-5: 6.35, dd; H-6: 6.83, d; H-8: 4.10, dd; H-16: 3.88, m; CO—NH—: 5.35, d; cyclohexil-CH: 3.75, m, 1H $^{13}$C-NMR (CDCl$_3$; δ [ppm], $δ_{TMS}$=0; multiplicity): C-2: 76.8, d; C-4: 139.0, d; C-5: 126.7, d; C-6: 144.1, d; C-7:115.7, s; 7-CN: 118.2, s; C-8: 73.2, d; C-16: 69.7, d; C-18: 172.5, s; 1'-CO—NH—: 174.3, s; cyclohexil: 50.47, d; 33.3, t; 33.4, t; 25.3, t; 24.7, t; 24.8, t TS (EI, 70 eV; m/z): 570, [M]$^{+ \cdot}$; 552, [M—H$_2$O]$^{+ \cdot}$; 534, [M—2H$_2$O]$^{+ \cdot}$; 327, [C$_{20}$H$_{27}$N$_2$O$_2$]$^+$; 224, [C$_{13}$H$_{22}$NO$_2$]$^+$.

TS (CI, i-butane; m/z): 571, [M+H]$^+$; 553, [M+H—H$_2$O]$^+$.

EXAMPLE 14

Borrelidin-1-ethanolamide [(I), R=CONH—CH$_2$CH$_2$OH]

To a mixed anhydride solution prepared from 200 mg (0.41 mmol) of borrelidin according to Example 3 124 μl (2 mmol, 125 mg) of ethanolamine were added. After stirring for 3 hours, the starting borrelidin ($R_f$=0.43) disappeared and the product ($R_f$=0.26) appeared, which was proved by thin-layer chromatography (silica gel plate, eluent system: chloroform/methanol 95:5). The reaction mixture was evaporated to dryness. The dry residue was dissolved in 100 ml of chloroform, washed with 3×30 ml of water, dried over sodium sulfate and evaporated to dryness. The dry residue was chromatographed on a silica gel column with mixtures of chloroform and ethyl acetate of increasing ethyl acetate content. The fractions containing the product eluting with a 3:7 eluting mixture were combined and evaporated to dryness. The structure of the thus-obtained solidifying oily product (198 mg) was confirmed by spectroscopic (PMR, CMR, TS) data.

Characteristic Spectral Data

IR: 3350; 2958; 2212; 1719; 1646 cm$^{-1}$ $^1$H-NMR (CDCl$_3$; δ [ppm], $δ_{TMS}$=0; multiplicity): H-2: 4.98, dt; H-4: 6.28, m; H-5: 6.38, dd; H-6: 6.83, d; H-8: 4.10, d; H-16: 3.82, m; CO—NH—CH$_2$: 6.32, t; NH—CH$_2$—CH$_2$—: 3.38, m; CH$_2$—CH$_2$—OH: 3.70, m $^{13}$C-NMR (CDCl$_3$; δ [ppm], $δ_{TMS}$=0; multiplicity): C-2: 76.7, d; C-4: 139.0, d; C-5: 126.6, d; C-6: 144.1, d; C-7: 115.6, s; 7-CN: 118.4, s; C-8: 73.1, d; C-16: 69.4, d; C-18: 172.3, s; 1'-CO—NH—: 176.7, s; NH—CH$_2$—CH$_2$: 42.3, t; CH$_2$—CH$_2$—OH: 61.7, t TS (EI, 70 eV; m/z): 532, [M]$^{+ \cdot}$; 514, [M—H$_2$O]$^{+ \cdot}$; 496, [M—H$_2$O]$^{+ \cdot}$; 478, [M—3H$_2$O]$^{+ \cdot}$; 289, [C$_{16}$H$_{21}$N$_2$O$_3$]$^+$; 271, [C$_{16}$H$_{19}$N$_2$O$_2$]$^+$; 186, [C$_9$H$_{16}$NO$_3$]$^+$.

TS (CI, i-butane; m/z): 533, [M+H]$^+$; 515, [M+H—H$_2$O]$^+$.

EXAMPLE 15

Borrelidin-3-picolylamide [(I), R=CONHCH$_2$—C$_5$H$_4$N]

To a mixed anhydride solution prepared from 4.0 g (8.2 mmol) of borrelidin according to Example 34.2 ml (41.2 mmol, 4.46 g) of 3-picolylamine were added. After stirring for 3 hours, the starting borrelidin ($R_f$=0.43) disappeared and the product ($R_f$=0.24) appeared, which was proved by thin-layer chromatography (silica gel plate, eluent system: chloroform/methanol 95:5). The reaction mixture was evaporated to dryness. The dry residue was dissolved in 500 ml of chloroform, washed with 3×1500 ml of water, dried over sodium sulfate and evaporated to dryness. The dry residue was chromatographed on a silica gel column with mixtures of chloroform and ethyl acetate of increasing ethyl acetate content. The fractions containing the product eluting with a 2:8 eluting mixture were combined and evaporated to dryness. To the thus-obtained solidifying oily substance (3.62 g) 4 ml of ethyl acetate and 20 ml of n-hexane were added, the solid material was triturated and then filtered. In this way 3.04 g product were obtained. Mp.: 99–105° C.

Elementary analysis for C$_{34}$H$_{49}$N$_3$O$_5$ (M: 579.785):

calculated: C=70.43%, H=8.52%, N=7.25%, found; C=70.45%, H=8.88%, N=6.91%.

UV: $λ_{max}$ (EtOH)=256 nm (ε=29166).

The structure of the product was proved by spectroscopic (PMR, CMR, TS) data.

Characteristic Spectral Data

IR: 3325; 2958; 2212; 1732; 1651; 1251 cm$^{-1}$ $^1$H-NMR (CDCl$_3$; δ [ppm], δ$_{TMS}$=0; multiplicity): H-2: 4.98, dt; H-4: 6.22, m; H-5: 6.39, dd; H-6: 6.81, d; H-8: 4.10, d; H-16: 3.80, m; 1'-CONH—: 6.50, t; NH—CH$_2$-3Py: 4.25, dd and 4.60, dd; Py: 7.25, dd; 7.63, d and 8.43–8.53, m, 2H $^{13}$C-NMR (CDCl$_3$; δ [ppm], δ$_{TMS}$=0; multiplicity): C-2: 76.5, d; C-4: 138.7, d; C-5: 126.7, d; C-6: 144.0, d; C-7: 116.0, s; 7-CN: 118.5, s; C-8: 73.0, d; C-16: 69.7, d; C-18: 172.2, s; 1'-CO—NH—: 175.8, s; NH—CH$_2$-3Py: 41.1, t; y: 148.8, d; 134.2, s; 135.7, d; 123.6, d; 148.6, d TS (EI, 70 eV; m/z): 579, [M]$^{+\cdot}$; 561, [M—H$_2$O]$^{+\cdot}$; 336, [C$_{20}$H$_{22}$N$_3$O$_2$]$^+$; 107, [C$_6$H$_7$N$_2$]$^+$; 93 [C$_6$H$_7$N]$^{+\cdot}$; 92, [C$_6$H$_6$N]$^+$.

TS (CI, i-butane; m/z): 580, [M+H]$^+$.

Preparation of the Hydrochloride Salt 350 mg (0.6 mmol) of the above product were dissolved in 5 ml of tetrahydrofuran, then 70 μl of a 37% aqueous hydrochloric acid solution were added at 0° C. under stirring. The solvent was evaporated under vacuo and the water was removed by azeotropic distillation with benzene. The dry residue was triturated with absolute ether. The solid material was filtered and washed with ether. In this way 330 mg of product were obtained. Mp.: 114–118° C.

Elementary analysis for C$_{34}$H$_{49}$N$_3$O$_5$·HCl·2H$_2$O (M: 652.246):

calculated: C=62.61%, H=8.35%, N=6.44%, Cl=5.44%, H$_2$O=5.52%; found: C=64.16%, H=8.22%, N=6.44%, Cl=5.67%, H$_2$O=5.57%.

UV: λ$_{max}$ (EtOH)=256 nm (ε=30170).

Characteristic Spectral Data $^1$H-NMR (DMSO-d$_6$, δ [ppm], δ$_{TMS}$=0; multiplicity): H-2: 4.85, dt; H-4: 6.30, m; H-5: 6.48, dd; H-6: 6.95, d; H-8: 4.08, d; H-16: 3.70, m; 1'-CONH—: 8.60, t; NH—CH$_2$-3Py: 4.26, dd and 4.54, dd; Py: 7.92, dd; 8.30, d and 8.68–8.82, m, 2H $^{13}$C-NMR (DMSO-d$_6$, δ [ppm], δ$_{TMS}$=0; multiplicity): C-2: 75.6, d; C-4: 139.1, d; C-5: 127.5, d; C-6: 143.4, d; C-7: 116.6, s; 7-CN: 119.4, s; C-8: 70.8, d; C-16: 70.0, d; C-18: 171.1, s; 1'-CO—NH—: 175.9, s; NH—CH$_2$-3Py: 38.2, t; Py: 143.4, d; 141.5, d; 141.3, d; 139.3, s; 126.6, d

What is claimed is:

1. A compound having the formula (I):

wherein:

R is —COOR$^1$, —CONR$^2$R$^3$ or CONR$^4$CONR$^4$R$^5$;

R$^1$ is:

C$_{1-6}$ alkyl, substituted by a member selected from the group consisting of: hydroxyl; amino; di(C$_{1-4}$ alkyl) amino; a 5- to 8-membered saturated, nitrogen-containing heterocyclic ring, optionally having, in addition to the required nitrogen ring atom, an oxygen ring atom or one or two further nitrogen ring atoms; and a 5- or 6-membered nitrogen-containing aromatic heterocyclic ring optionally having, in addition to the required nitrogen ring atom, an oxygen ring atom or one or two further nitrogen ring atoms; or C$_{3-6}$ cycloalkyl;

R$^2$ and R$^3$ are identical or different and independently from each other represent:

hydrogen;

C$_{1-6}$ alkyl, optionally substituted by a member selected from the group consisting of: halogen; hydroxyl; amino; C$_{2-5}$ alkoxycarbonyl; di(C$_{1-4}$ alkyl)amino; a 5- to 8-membered saturated, nitrogen-containing heterocyclic ring, optionally having, in addition to the required nitrogen ring atom, an oxygen ring atom or one or two further nitrogen ring atoms; a phenyl ring; and a 5- or 6-membered aromatic heterocyclic ring having an oxygen ring atom and/or a nitrogen ring atom; or a 5- or 6-membered cycloalkyl ring or a 5- or 6-membered aromatic heterocyclic ring having an oxygen ring atom and/or a nitrogen ring atom; and R$^4$ and R$^5$ are identical or different and independently from each other represent hydrogen, C$_{1-6}$ alkyl, C$_{3-6}$ cycloalkyl or phenyl;

or a tautomer, solvate, mixture or acid addition salt thereof.

2. A compound selected from the group consisting of:

2'-(7-cyano-8,16-dihydroxy-9,11,13,15-tetramethyl-18-oxo-oxacyclooctadeca-4,6-dien-2-yl)cyclopentane-1'-carboxylic acid 3-pyridinemethanamide and the acid addition salts thereof;

2'-(7-cyano-8,16-dihydroxy-9,11,13,15-tetramethyl-18-oxo-oxacyclooctadeca-4,6-dien-2-yl)-cyclopentane-1'-carboxylic acid 2-pyridinemethanamide and the acid addition salts thereof;

2'-(7-cyano-8,16-dihydroxy-9,11,13,15-tetramethyl-18-oxo-oxacyclooctadeca-4,6-dien-2-yl)-cyclopentane-1'-carboxylic acid amide; and 2'-(7-cyano-8,16-dihydroxy-9,11,13,15-tetramethyl-18-oxo-oxacyclooctadeca-4,6-dien-2-yl)-cyclopentane-1'-carboxylic acid N,N-dicyclohexylcarbamidoamide.

3. The compound 2'-(7-cyano-8,16-dihydroxy-9,11,13,15-tetramethyl-18-oxo-oxacyclooctadeca-4,6-dien-2-yl)-cyclopentane-1'-carboxylic acid 3-pyridinemethanamide or its hydrochloride salt.

4. A pharmaceutical composition comprising as active ingredient a compound of formula (I) as claimed in claim 1 or a tautomer or therapeutically acceptable acid addition salt thereof, and a pharmaceutically acceptable carrier, dissolving agent, diluting agent and/or filling agent.

5. A method for the treatment of an angiogenic disease in a mammal which is caused by excessive, inappropriate angiogenesis, which comprises administering to a mammal in need of such treatment an effective angiogenesis-inhibiting dosage amount of a compound as defined in claim 1.

6. A method for the treatment of an angiogenic disease in a mammal which is caused by excessive, inappropriate angiogenesis, which comprises administering to a mammal in need of such treatment an effective angiogenesis-inhibiting dosage amount of a compound as defined in claim 2.

7. A method for the treatment of an angiogenic disease in a mammal which is caused by excessive, inappropriate angiogenesis, which comprises administering to a mammal in need of such treatment an effective angiogenesis-inhibiting dosage amount of the compound or salt as defined in claim 3.

* * * * *